US00PP26809P3

(12) United States Plant Patent
Klemm et al.

(10) Patent No.: US PP26,809 P3
(45) Date of Patent: Jun. 7, 2016

(54) ***BEGONIA* PLANT NAMED 'KLEBG13465'**

(50) Latin Name: ***Begonia* sp.**
Varietal Denomination: KLEBG13465

(71) Applicant: Klemm+Sohn GmbH & Co. KG, Stuttgart (DE)

(72) Inventors: Nils Klemm, Stuttgart (DE); Silke Wagener, Leinfelden-Echterdingen (DE)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 135 days.

(21) Appl. No.: 14/120,250

(22) Filed: May 13, 2014

(65) Prior Publication Data

US 2015/0334901 P1 Nov. 19, 2015

(51) Int. Cl.
*A01H 5/02* (2006.01)

(52) U.S. Cl.
USPC ..... Plt./343

(58) Field of Classification Search
USPC ..... Plt./343
See application file for complete search history.

*Primary Examiner* — Keith Robinson
(74) *Attorney, Agent, or Firm* — James M. Weatherly; Bethany R. Roahrig; Cochran Freund & Young, LLC

(57) ABSTRACT

A new *Begonia* plant particularly distinguished by having an orange-red flower color and dark green leaves, is disclosed.

1 Drawing Sheet

Genus and species: *Begonia* sp.
Variety denomination: 'KLEBG13465'.

BACKGROUND OF THE NEW PLANT

The present invention comprises a new and distinct variety of *Begonia*, botanically known as *Begonia* sp. and hereinafter referred to by the variety name 'KLEBG13465'. 'KLEBG13465' is a selection from a cross-pollination of the proprietary female *Begonia* line 'PL 01' (unpatented) and the proprietary male *Begonia* line 'YA 01' (unpatented).

Between June 2009 and July 2009 the proprietary female *Begonia* line 'PL 01' and the proprietary male *Begonia* line 'YA 01' were cross-pollinated in Stuttgart, Germany and seeds were obtained. The seeds were sown and plants were grown for evaluation. A plant line was selected between May 2010 and June 2010 in Stuttgart, Germany and named 'KLEBG13465'. In June 2010, 'KLEBG13465' was first vegetatively propagated by vegetative stem tip cuttings. 'KLEBG13465' was found to reproduce true to type in successive generations of asexual propagation via vegetative stem tip cuttings in Stuttgart, Germany.

SUMMARY

The following are the most outstanding and distinguishing characteristics of this new variety when grown under normal horticultural practices in Stuttgart, Germany.

1. Orange-red flower color; and
2. Dark green leaves.

DESCRIPTION OF THE PHOTOGRAPH

This new *Begonia* plant is illustrated by the accompanying photograph which shows an overall view of a five to six month old plant taken in Stuttgart, Germany in July of 2013. The colors shown are as true as can be reasonably obtained by conventional photographic procedures.

DESCRIPTION OF THE NEW VARIETY

The following detailed descriptions set forth the distinctive characteristics of 'KLEBG13465'. The data which define these characteristics were collected from asexual reproductions carried out in Stuttgart, Germany. Data was collected on three month-old plants grown in controlled greenhouse conditions using natural and artificial light in Stuttgart, Germany in January of 2014. The plants were pinched one time and no growth regulator was used. Color references are to The R.H.S. Colour Chart of The Royal Horticultural Society of London (R.H.S.), 5$^{th}$ edition (2007).

Classification:
- *Family*.—Begoniaceae.
- *Species*.—*Begonia* sp.
- *Common name*.—*Begonia*.
- *Variety*.—'KLEBG13465'.

Parentage:
- *Female*.—Proprietary *Begonia* line 'PL 01'.
- *Male*.—Proprietary *Begonia* line 'YA 01'.

Plant:
- *Form*.—Compact.
- *Habit*.—Upright and mounded plant habit, freely branching.
- *Plant height*.—About 15.0 cm.
- *Plant width*.—About 30.0 cm.
- *Flowering habit*.—Single flowers.
- *Time to produce a finished flowering plant*.—2 to 3 months.
- *Propagation type*.—Vegetative stem tip cutting.
- *Time to initiate roots*.—About 2 weeks.
- *Root description*.—Freely branching, white to brown in color, between RHS 155A and RHS 158A.

Lateral branches:
- *Quantity per plant*.—4 to 6 basal branches.
- *Color*.—RHS 138A and RHS 184B upper nodes.
- *Length*.—About 10.0 cm to 14.0 cm.
- *Diameter*.—About 0.5 cm to 1.0 cm.
- *Internode length*.—About 2.0 to 3.0 cm.
- *Texture*.—Pubescent (covering of fine colorless hairs).
- *Anthocyanin*.—Some anthocyanin on the upper nodes.
- *Anthocyanin color*.—RHS 176C.

Leaves:

*Arrangement*.—Alternate.

*Length*.—About 8.0 cm.

*Width*.—About 4.0 cm to 5.0 cm.

*Shape*.—Lanceolate, strongly asymmetric with one side ovate.

*Apex*.—Acuminate.

*Base*.—Oblique, cordate.

*Margin*.—Serrate with short bristles emerging from tip of the teeth.

*Texture*.—Smooth, low surface sparsely covered with hairs.

*Color*.—Immature leaf: Upper surface: RHS 136A, around veins RHS 143C, very early stages have some anthocyanin. Lower surface: RHS 187C, veins RHS 139D. Mature leaf: Upper surface: RHS 136A, around veins RHS 139C. Lower surface: RHS 184C, around veins RHS 147C.

*Venation pattern*.—Pinnate and palmate.

*Venation color*.—Immature leaf: Upper surface: RHS 143C. Lower surface: RHS 139D. Mature leaf: Upper surface: RHS 139C. Lower surface: RHS 147C.

*Petiole*.—Length: Up to 6.0 cm. Diameter: 0.3 cm. Color: RHS 176C. Texture: Pubescent (covering of fine colorless hairs).

Flowers:

*Inflorescence type*.—Single flowers arranged in axillary cymes.

*Quantity of flowers per cyme*.—1 to 2.

*Quantity of cymes per plant*.—About 10 (3 month old plants).

*Flowering season*.—Spring to autumn.

*Lastingness of individual flowers on the plant*.—About 1 to 2 weeks.

*Fragrance*.—Absent.

*Bracts*.—Quantity per flower: 2. Length: About 0.6 cm. Width: Abut 1.0 cm. Shape: Round. Apex: Acute. Base: Rotundate. Margin: Shallow. Color: Upper surface: RHS 145B, with RHS 48B at the apex. Lower surface: RHS 145C, with RHS 48B at the apex.

*Peduncle*.—Length: 8.0 cm. Diameter: 0.2 cm. Color: RHS 179A. Texture: Smooth.

*Female flowers*.—Bud: Shape: Flattened ovate. Height: About 2.0 cm. Width: About 1.2 cm. Color: RHS 31B. Texture: Smooth. Flowers: Single. Shape: Radial bell-mouthed. Depth/Height: 3.0 cm. Width: 5.0 cm. Tepals: Quantity per flower: 5 total; 3 outer and 2 inner. Inner tepals: Shape: Reverse lanceolate. Length: 3.0 cm. Width: 1.2 cm. Color: Upper surface: RHS 30B. Lower surface: RHS 32B. Texture: Smooth. Outer tepals: Shape: Ovate, rotundate base, obtuse apex. Length: 3.0 cm. Width: 2.0 cm. Color: Upper surface: RHS 30B. Lower surface: RHS 32B. Texture: Smooth. Pedicel: Length: 3.0 to 4.0 cm. Diameter: About 0.1 cm. Color: RHS 179B. Texture: Smooth.

*Male flowers*.—Flowers: Single. Shape: Bilateral bell-mouthed. Depth/Height: 3.0 cm. Width: 4.0 cm. Tepals: Quantity per flower: 4 total; 2 outer and 2 inner. Inner tepals: Shape: Reverse lanceolate. Length: 3.5 cm. Width: 1.2 cm. Color: Upper surface: RHS 30B. Lower surface: RHS 32B. Texture: Smooth. Outer tepals: Shape: Ovate, rotundate base, obtuse apex. Length: 3.0 cm. Width: 2.5 cm. Color: Upper surface: RHS 30B. Lower surface: RHS 32B. Texture: Smooth. Pedicel: Length: About 3.0 cm to 4.0 cm. Diameter: About 0.1 cm. Color: RHS 179B. Texture: Smooth.

Reproductive organs:

*Stamens* (*on the male flowers*).—Quantity per male flower: 30 to 35. Anther shape: Lanceolate. Anther length: 0.15 cm. Anther color: RHS 17B. Pollen amount: Moderate. Pollen color: RHS 8C.

*Pistils* (*on the female flowers*).—Quantity per female flower: 3. Pistil length: About 1.5 cm. Style length: 0.5 cm (including extension). Style color: RHS 30B. Stigma shape: Bifid, twisted around extensions of the style. Stigma color: RHS 17A. Ovary color: RHS 145A, tips RHS 41B.

Fruit and seed set: None observed.

Disease and insect resistance: No particular disease or insect resistance observed.

COMPARISON WITH PARENTAL LINES AND KNOWN VARIETY

'KLEBG13465' is a distinct variety of *Begonia*. 'KLEBG13465' is distinguished from its parents as described in Table 1:

TABLE 1

Comparison with Parental Lines

| Trait or characteristic | Variety 'KLEBG13465' | Female parent 'PL 01' | Male Parent 'YA 01' |
|---|---|---|---|
| Leaf color | Dark green | Green | Green |
| Flower color | Orange-red | Red | Red |

'KLEBG13465' is most similar to the commercial *Begonia* plant named 'KLEBG14477' (U.S. Plant Pat. application Ser. No. 14/120,251). Differences between the two varieties are described in Table 2:

TABLE 2

Comparison with Similar Variety

| Trait or characteristic | Variety 'KLEBG13465' | Commercial line 'KLEBG14477' |
|---|---|---|
| Flower color | Orange-red | Red |

We claim:

1. A new and distinct variety of *Begonia* plant named 'KLEBG13465' as illustrated and described herein.

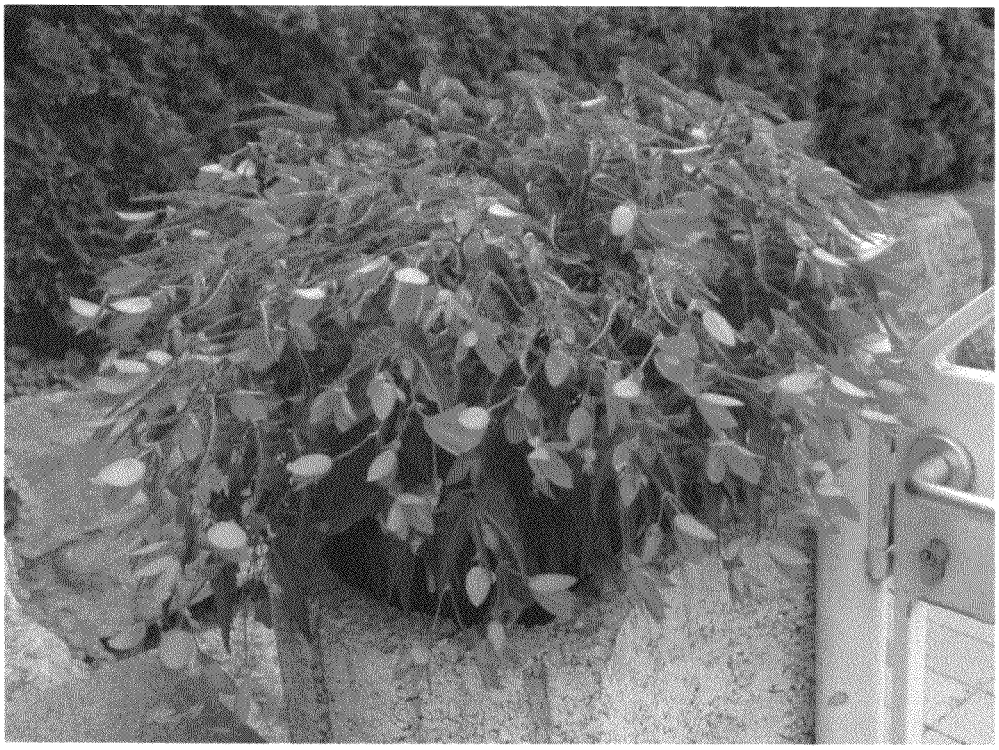

* * * * *